United States Patent [19]

Wharton

[11] 4,066,419

[45] Jan. 3, 1978

[54] GASOLINE COMPOSITIONS

[75] Inventor: David G. Wharton, Upton-by-Chester, England

[73] Assignee: Shell Oil Company, Houston, Tex.

[21] Appl. No.: 740,170

[22] Filed: Nov. 8, 1976

[30] Foreign Application Priority Data

Dec. 19, 1975 United Kingdom ............... 52100/75

[51] Int. Cl.$^2$ ............................................. C10L 1/26
[52] U.S. Cl. ..................................................... 44/72
[58] Field of Search ....................... 44/76, 72; 260/944

[56] References Cited

U.S. PATENT DOCUMENTS

| | | | |
|---|---|---|---|
| 3,094,547 | 6/1963 | Heine | 252/46.7 |
| 3,250,600 | 5/1966 | Ballard et al. | 44/72 |
| 3,374,072 | 3/1968 | Deffner | 44/72 |
| 3,652,238 | 3/1972 | Bialy et al. | 44/72 |
| 3,911,056 | 10/1975 | Houghton | 260/944 |
| 3,970,586 | 7/1976 | Schliebs et al. | 260/944 |

Primary Examiner—Daniel E. Wyman
Assistant Examiner—Mrs. Y. Harris-Smith
Attorney, Agent, or Firm—Ronald R. Reper

[57] ABSTRACT

Gasoline compositions having improved driveability comprise gasoline containing a minor amount of a compound having the formula

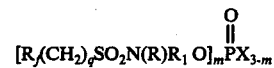

$$[R_f(CH_2)_qSO_2N(R)R_1O]_mPX_{3-m}$$

wherein $R_f$ is a perfluorinated radical selected from the group consisting of aliphatic $C_nF_{2n+1}$ and cycloaliphatic $C_nF_{2n-1}$, $n$ is an integer from 1 – 18, $q$ is 0 or an integer from 1 to 18, R is hydrogen or an alkyl radical having from 1 to 12 carbon atoms, $R_1$ is an alkylene bridging radical having from 2 to 12 carbon atoms, $m$ is 1 or 2, and X is chlorine, hydroxyl, —OMe (where Me is a metal), or a residual moiety of an active hydrogen-containing organic compound.

9 Claims, 1 Drawing Figure

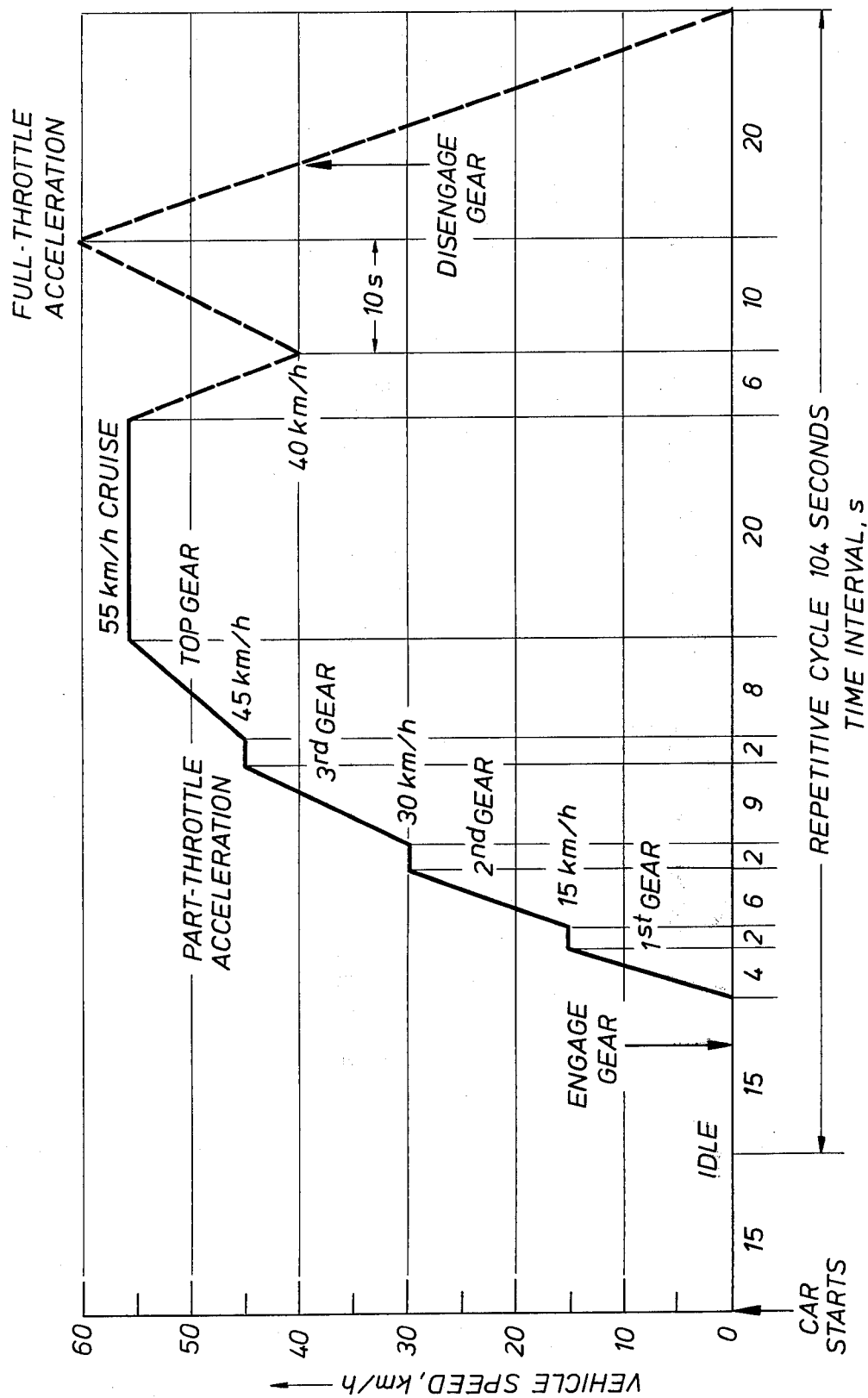

GASOLINE COMPOSITIONS

BACKGROUND OF THE INVENTION

The invention relates to gasoline compositions having improved driveability in a spark-ignited engine.

As is known, inherent in the conventional carburetted multi-cylinder automobile engine are various factors which influence the driveability of the automobile. One such principal factor is the distribution of the air/fuel mixture to the various cylinders through the intake manifold.

In the past any problems arising from the distribution of the fuel in the induction system of the automobile engine has been mitigated or solved by operating the engine on a richer air/fuel mixture, one having a greater than stoichiometric mixture for complete combustion. This mixture was chosen to obtain maximum power with maximum fuel economy.

In order to comply with legislative controls for automotive emission, automotive manufacturers now design automobile engines to operate on leaner air/fuel ratios approaching the stoichiometric mixture, that is, one containing the chemically correct proportions of fuel and air for complete combustion. Although operating with these leaner ratios helps hydrocarbon and carbon monoxide emissions, the problem of cylinder-to-cylinder distribution of the fuel/air mixture is accentuated and it is no longer possible to solve this distribution problem by using richer air/fuel mixtures. Although this lean carburation is a principal factor, it is not the only cause for poor driveability.

Additionally, the engine warm-up period immediately subsequent to cold start is very difficult to control and in the past the choke control was used for a longer period in order to improve driveability during the warm-up period. However, in order to cut back on exhaust emissions, longer choke periods are no longer permissible and the resulting leaner air/fuel mixture used during the warm-up cycle has also accentuated the driveability problem.

The partially-oxidized metal layers comprising the carburetor and intake manifold interior surfaces have critical surface tension and wettability and are completely wetted by any hydrocarbon gasoline component, especially the aliphatic and/or aromatic components. The mixture of gasoline and air that leaves the carburetor and passes to the various cylinders through the intake manifold thereby tends to deposit some of the higher boiling fractions particularly rich in aromatics in the form of a liquid film on these surfaces and particularly on the walls of the intake manifold. For the best distribution of the fuel in the induction system, the gasoline should be present as a vapor or a mist in the air/fuel mixture; therefore, wetting of this surface contributes to less satisfactory distribution and poor driveability.

It has now been found that certain organic compounds which contain fluorine, phosphorus and sulfur inhibit the wetting of the walls of the inlet manifold by gasoline and have a favorable influence on the distribution of the air/fuel mixture to the various cylinders of a multicylinder internal combustion engine.

SUMMARY OF THE INVENTION

According to the invention there is provided a gasoline composition comprising a major proportion of gasoline and a minor amount of a compound having the formula

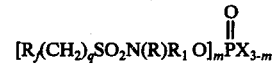

wherein $R_f$ is a perfluorinated radical selected from the group consisting of aliphatic $C_nF_{2n+1}$ and cycloaliphatic $C_nF_{2n-1}$, $n$ is an integer from 1 - 18, $q$ is 0 or an integer from 1 to 18, R is hydrogen or an alkyl radical having from 1 to 12 carbon atoms, $R_1$ is an alkylene bridging radical having from 2 to 12 carbon atoms, $m$ is 1 or 2, and X is chlorine, hydroxyl, —OMe (where Me is a metal) or a residual moiety of an active hydrogen-containing organic compound.

The invention further provides a method for improving the operation of a spark-ignited engine which comprises operating said engine with said gasoline composition.

BRIEF DESCRIPTION OF THE DRAWING

The sole FIGURE is a diagrammatic illustration of the test cycle of modes of engine operation used to rate driveability in the working example.

DESCRIPTION OF PREFERRED EMBODIMENTS

Preference is given to perfluorinated radicals $R_f$ having 5-12 carbon atoms, and particularly to $C_8F_{17}$. The $R_f$ radical may contain a branched carbon chain, however a straight carbon chain is preferred.

Very suitably $q$ is zero (in case it is 3 or more $(CH_2)_q$ may comprise a straight or branched chain of carbon atoms), and R is an alkyl radical having from 1 to 6 carbon atoms.

$R_1$ preferably contains 2 to 8 carbon atoms, it may be branched or straight chain, and very suitably is an ethylene group.

The term "active hydrogen atoms" is that which is understood in the Tschugaeff-Zerewitinoff analytical technique, see e.g. J. Am. Chem. Soc. 49, 2181 (1927). Residual moieties with active hydrogen atoms are e.g. amino-, alkoxy- and aralkoxy groups.

Suitable examples of these compounds are N-ethyl perfluoroctanesulfonamidoethyl phosphoryl dichloridate, mono-(N-hexylperfluorodecanesulfonamidoethyl) phosphate, bis-(N-propyl-perfluorocyclohexanesulfonamidoethyl) phosphate, mono-(perfluorohexanesulfonamidobutyl) phosphate, bis-(N-ethyl perfluoroethylcyclohexanesulfonamidoethyl) phosphate, di-phenyl (N-hexyperfluorocyclohexanesulphonamidoethyl) phosphate, and N'-ethyl, N''-ethyl (N-ethyl perfluorooctanesulfonamidoethyl) phosphorodiamidate, and in particular mono-(N-ethyl perfluorooctanesulfonamidoethyl) phosphate.

The amounts of fluorinated compound present in the gasoline compositions according to the invention may vary between wide limits; amounts from about 1 to about 60 parts per million w/v, i.e. about 0.25 to about 15 pounds per thousand barrels of gasoline, are very suitable. Preferably the amounts will vary in the range from about 4 to about 50 parts per million w/v.

The base component of the novel gasoline compositions according to the invention is the motor fuel, gasoline. As is well known in the art, gasoline can be defined as a mixture of hydrocarbons of various boiling points and having a boiling range determined according to ASTM Method D-86 between about 20° and 230° C. Gasoline in general contains from about 0 to about 30% by volume of olefins, from about 5 to about 55%, preferably from about 10 to about 45%, by volume of aromatics, and the remainder, saturates.

An unexpected result from the use of the novel gasoline compositions of the invention is one which is especially advantageous in light of projected lower growth rate of available hydrocarbon supplies as compared with growth in demand for hydrocarbons. In order to improve the driveability of an engine heretofore, more volatile hydrocarbon components were blended with the gasoline. By improving the driveability using the gasoline compositions of the invention rather than by hydrocarbon blending, light hydrocarbons in an amount of up to about 2% by volume of gasoline can be more effectively utilized elsewhere, e.g. in the petrochemical field. In a market as large as the gasoline market, such diversion is of considerable importance.

The gasoline compositions of the invention may contain additionally other additives which are well known in the art. Alkyl head antiknock agents such as tetraethyl lead, tetramethyl lead and the like may be present along with customarily employed scavenging agents such as ethylene dibromide in concentrations producing either "conventionally leaded" or low-lead gasoline as is known in the art. However, lead compounds need not be present and may be absent to the extent required for maintaining the gasoline compositions of the invention as unleaded gasoline. Organo-metallic antiknock agents other than lead compounds such as methylcyclopentadienyl manganese tricarbonyl may be employed also. Other additives conventionally employed in gasoline may be used in practicing the present invention. These include corrosion or rust inhibitors, antioxidants, solvent oils, metal deactivators, anti-icing agents, dyes and the like. There may also be included nitrogen-containing gasoline detergent/dispersant additives such as those described in U.K patent specifications Nos. 1,094,020 and 1,309,907.

In order to rate driveability, test procedures have been developed in which various elements of driveability are measured and ratings are given in the form of demerits. The demerits are then weighted according to a weighting factor. In the test used in the following Example the procedure involves driving a test cycle on a chassis dynamometer which includes those modes of operation defined as being the most common driveability problem areas: part-throttle acceleration through the gears, full-throttle acceleration, light-throttle cruise and idle. The test cycle is represented in the FIGURE. The performance is subjectively rated by the driver in the terms of occurrence and severity of hesitations and stumbles for the accelerations, surge (which is a low-frequency velocity oscillation of the vehicle under steady-speed cruise conditions) for the cruise, backfire, and the occurrence of driving stall and start stall. Idle quality is also taken into account. A rating scale as depicted in Table I is used for the individual malfunctions, and from this scale a weighted sum of demerits is calculated for ten cycles and is defined as the driveability of the vehicle for the given ambient temperature and fuel.

The percentage of improvement of the total demerits for a certain car measured with a gasoline with and without a driveability improving additive, can equivalently be expressed as the apparent change in mid-point volatility ($\Delta T$ 50% E) of the gasoline used. "$\Delta T$ 50% E" is the change in mid-point volatility of the gasoline which would cause a similar driveability improvement; it is calculated from fuel volatility sensitivity tests assuming linear variation over a range of midpoints of 95° C to 109° C. The $\Delta T$ 50% E enables the use of gasoline with a smaller proportion of low boiling components in the gasolines compositions according to the invention, which is of considerable advantage as has been discussed above.

EXAMPLE

The tests were carried out on a chassis dynamometer with 10 test cycles as discussed above at an ambient temperature of 0° C. A Morris Marina 1.8 and a Datsun 160 B were used as test vehicles. The gasoline compositions used contained 30 ppm of mono-(N-ethylperfluorooctane-sulfonamidoethyl) phosphate. The inlet manifolds were pretreated with an acetone solution of this compound. The demerits were determined versus the use of undoped gasoline and non-pretreated inlet manifolds.

Table II gives the results; HBS demerits stands for demerits in hesitation, stumble and backfire. As can be seen appreciable improvements in driveability and warm-up time are achieved. Warm-up time is defined as being the time to achieve a full-throttle acceleration rate equivalent to 70% that obtained on a reference fuel with a fully warmed-up vehicle.

Table I
Driveability demerit scale

| Malfunction | Driveability demerits | | | | Demerit weighting factor |
|---|---|---|---|---|---|
| | Trace | Moderate | Heavy | Yes | |
| Idle roughness | 1 | 2 | 3 | — | 1 |
| Hesitation | 1 | 3 | 6 | — | 4 |
| Stumble | 1 | 3 | 6 | — | 4 |
| Surge | 1 | 2 | 3 | — | 3 |
| Stall at start | — | — | — | 6 | 3 |
| Driving stall | — | — | — | 6 | 7 |
| Backfire | 1 | 2 | 3 | — | 4 |

Table II

| | Morris Marina 1.8 | Datsun 160B |
|---|---|---|
| Total demerits | 35% | 21% |
| (Equiv. $\Delta T50\%E$) | (6¼% C) | (—) |
| HSB demerits | 37% | 22% |
| (Equiv. $\Delta T50\%E$) | (6° C) | (5° C) |
| Warm-up time | 28% | 16% |
| (Equiv. $\Delta T50\%E$) | (9¼° C) | (7° C) |

What is claimed is:

1. A gasoline composition comprising a minor proportion of gasoline and from about 60 parts per million N/V of gasoline of compound having the formula:

wherein $R_f$ is a perfluorinated radical selected from the group consisting of aliphatic $C_nF_{2n+1}$ and cycloaliphatic $C_nF_{2n-1}$, $n$ is an integer from 1 – 18, $q$ is 0 or an integer from 1 to 18, R is hydrogen or an alkyl radical having from 1 to 12 carbon atoms, $R_1$ is an alkylene bridging radical having from 2 to 12 carbon atoms, $m$ is 1 or 2, and X is chlorine, hydroxyl, —OMe where Me is a metal, or a residual moiety of an active hydrogen-containing organic compound.

2. The gasoline composition of claim 1 wherein the perfluorinated radical $R_f$ contains from 5 to 12 carbon atoms.

3. The gasoline composition of claim 2 wherein $R_f$ is $C_8F_{17}$.

4. The gasoline composition of claim 2 wherein the perfluorinated radical $R_f$ comprises a straight carbon chain.

5. The gasoline composition of claim 2 wherein $q$ is 0.

6. The gasoline composition of claim 1 wherein R is an alkyl radical having from 1 to 6 carbon atoms.

7. The gasoline composition of claim 1 wherein $R_1$ contains from 2 to 8 carbon atoms.

8. The gasoline composition of claim 1 wherein the compound is mono-(N-alkylperfluorooctone-sulfonamidoethyl) phosphate.

9. The method of improving the operation of a spark-ignition engine which comprises operating said engine with the gasoline composition of claim 1.

* * * * *